United States Patent [19]

Harvey et al.

[11] Patent Number: 4,607,868

[45] Date of Patent: Aug. 26, 1986

[54] UNIVERSAL CONNECTOR

[75] Inventors: Roger W. Harvey, Vernon Hills, Ill.; Ralph Davis, Burlington, Wis.; Arthur Lueders, Mundelein; William J. Schnell, Libertyville, both of Ill.

[73] Assignee: Baxter Travenol Laboratories, Inc., Deerfield, Ill.

[21] Appl. No.: 556,504

[22] Filed: Nov. 30, 1983

[51] Int. Cl.⁴ .............................................. F16L 35/00
[52] U.S. Cl. ....................................... 285/332; 285/12; 285/3; 285/386; 285/423; 604/905; 604/241; 604/243; 604/244
[58] Field of Search ...................... 285/3, 12, 332, 386, 285/387, 423; 604/905, 283, 241, 242, 243, 272, 244

[56] References Cited

U.S. PATENT DOCUMENTS

| | | | |
|---|---|---|---|
| 2,455,667 | 12/1948 | Franck | 285/3 |
| 3,876,234 | 4/1975 | Harms | 285/332 X |
| 3,986,508 | 10/1976 | Barrington | 285/3 X |
| 4,296,949 | 10/1981 | Muetterties et al. | 285/18 |
| 4,346,703 | 8/1982 | Dennehey et al. | 128/213 A |
| 4,452,473 | 6/1984 | Ruschke | 285/332 X |

FOREIGN PATENT DOCUMENTS 2127866 10/1972 France ................................. 285/332

Primary Examiner—Richard J. Scanlan, Jr.
Attorney, Agent, or Firm—Paul C. Flattery; Garrettson Ellis; Daniel D. Ryan

[57] ABSTRACT

A universal connector for a fluid flow conduit comprises a tubular connector for attachment at one end to the fluid flow conduit and defining a luer taper tube portion at its other end. A sleeve is carried by and surrounding the tubular connector in relatively rotatable relation thereto. The sleeve defines internal threads for threaded locking connection with another connector. A tubular member having external threads at one end is locked by said external thread in removable threaded locking connection with the internal threads. The tubular member defines at its other end an aperture for sealingly receiving a spike connector.

6 Claims, 5 Drawing Figures

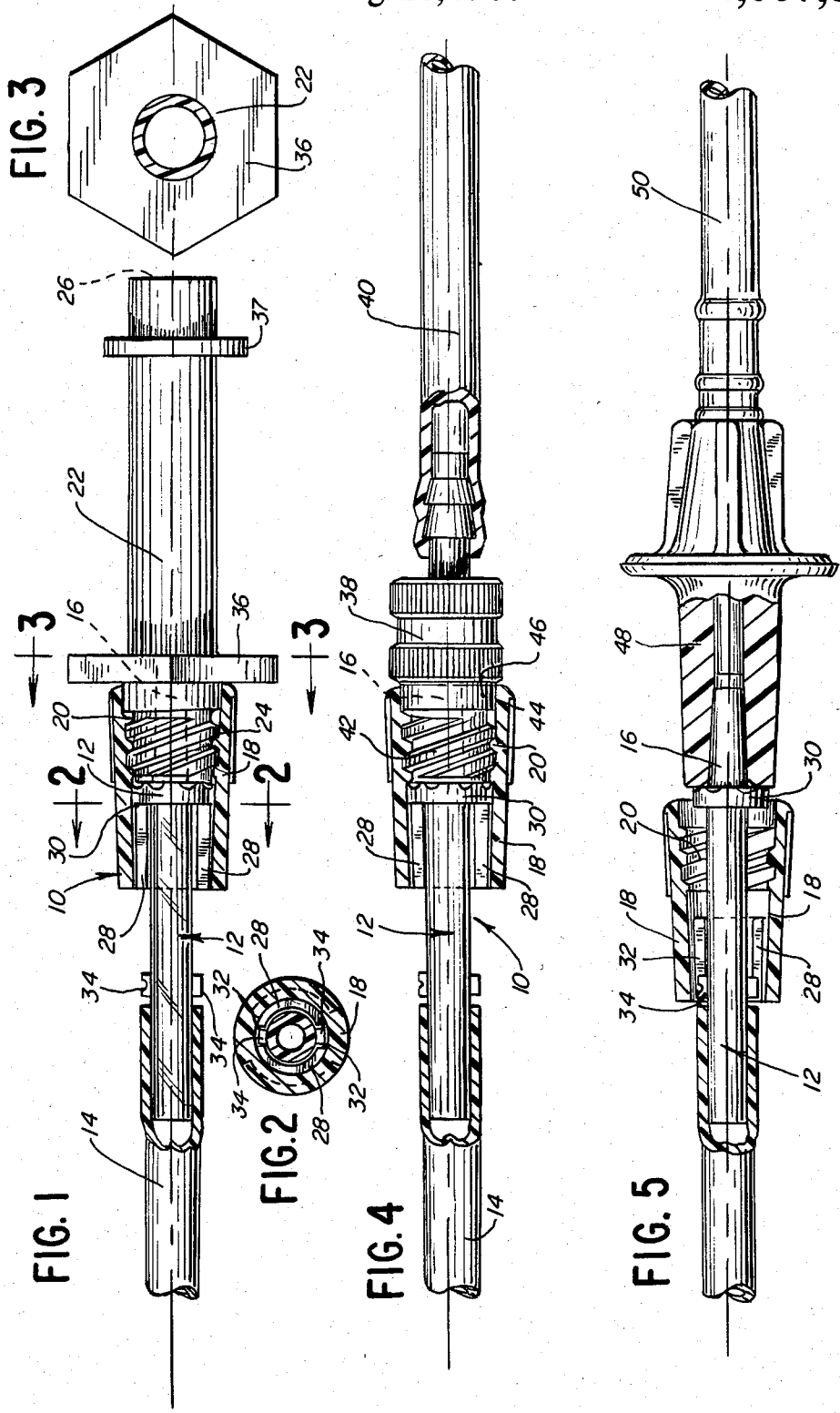

UNIVERSAL CONNECTOR

TECHNICAL FIELD AND PRIOR ART

This application relates to a universal connector for typically medical devices, although it may be used in any desired field. The connector is capable of providing sealed, reliable connection with (1) luer adapters of known design, (2) externally threaded connectors such as luer-lock connectors, and (3) spike connectors in which a hollow spike penetrates a sleeve in sealing relation thereto.

In the medical field, for example in the field of peritoneal dialysis, there are many different alternative modes of operation to accomplish a particular procedure.

In continuous ambulatory peritoneal dialysis (CAPD) the patient most commonly carries at all times a transfer set which communicates at one end with a catheter communicating, in turn, with the peritoneal cavity of the patient, with the transfer set having a spike connector at its other end.

Also, some common apparatus for CAPD makes use of a threaded connector called the "titanium adapter", which is carried at the end of the peritoneal catheter. It may be desirable to make a connection directly to the titanium adapter or other screw thread type connector.

Finally, many medical sets make connections through a simple luer connector, i.e., the well known tapered tube that fits into a tapered socket or luer adapter to provide a solid, frictional seal.

In the fields of continuous cycling peritoneal dialysis (CCPD), intermittent peritoneal dialysis (IPD), or the like it may be desirable in various circumstances to make use of various systems which have differing types of connectors as well.

To accommodate this, suppliers of equipment for dialysis and other medical procedures have been required to maintain a large number of different designs of medical sets, each carrying a different kind of connector: a screw thread connector, a luer, or a spike connector receiver, to accommodate the various needs and desires of the patients and their doctors. This results in a great proliferation of codes of product for sale, and designs of product, causing potential confusion, and significantly adding to the overall cost of the products, due to the complex administration of the large variety of codes and a loss of volume efficiencies in each individual code of product.

In accordance with this invention, a universal connector is proposed which is capable of several different types of connectors, for example for connection with acute catheters or chronic catheters. Through this, the number of designs and codes of products can be cut to one-third or less by the manufacturer, with resulting savings in cost of the product and the avoidance of confusion in ordering, inventory, shipping, and the like.

Accordingly, by this invention a patient on CAPD may be able to make connection with a set carrying the universal connector of this invention by connecting the spike on his transfer set to the connector. At the same time, the connector is capable of direct connection with a titanium adapter in screw threaded, luer lock relation. However, the connector is also capable of connection with a simple luer adapter, or an open catheter end. Accordingly, the patient finds himself capable of great flexibility of operation through the use of the universal connector of this invention, being able to switch his mode of dialysis treatment with great ease from CAPD to CCPD and back again, for example, as his desires and needs may dictate.

As prior art, the following pending patent applications relate to luer lock connectors having a locking sleeve with a "wrenching" action to assist in breaking of the luer connection when desired: Mittleman application Ser. No. 223,072, filed Jan. 6, 1981, and entitled "LUER LOCK CONNECTION"; Kersten application Ser. No. 409,276, filed Aug. 18, 1982, now abandoned, and entitled "LUER LOCK ADAPTER SYSTEM"; Ruschke application Ser. No. 401,571, filed July 26, 1982, now U.S. Pat. No. 4,452,473 and entitled "LUER CONNECTION SYSTEM"; and Ruschke application Ser. No. 401,572, filed July 26, 1982, now abandoned, and entitled "LUER CONNECTION SYSTEM WITH RESILIENT RING".

U.S. Pat. No. 4,346,703 discloses a locking connector having internal threads on a sleeve which are spaced from the free end of the sleeve to define an annular sealing area between the threads and the free end.

DESCRIPTION OF THE INVENTION

In accordance with this invention, a universal connector for a fluid flow conduit is disclosed. The connector comprises a tubular connector for attachment at one end to the fluid flow conduit, said tubular connector defining a luer taper tube portion at its other end for making connection with a luer adapter in generally conventional manner.

A sleeve is carried by the luer taper tube portion and fluid flow conduit in relatively longitudinally movable relation thereto. The sleeve defines internal threads for threaded locking connection with another connector. Thus the sleeve is capable of providing locking connection with another, externally threaded connector, for example the well known "titanium adapter" which is commonly used by peritoneal dialysis patients.

A tubular member is also provided having external threads at one end, with the external threads being in removable, threaded connection with the internal threads of the sleeve. The tubular member defines at its other end an aperture for sealingly receiving a spike connector.

The above described structure may be a part of a set, catheter, or container to facilitate connection with a number of different designs of other connectors. For example, the universal connector of this invention may be carried by a set for performing CCPD or IPD.

If one wishes to make connection to the universal connector with a spike connector, one can simply insert the spike through the aperture at the other end of the tubular member, where it forms a sealing spike connection. In the event one wishes to make connection with a luer lock connector such as the titanium adapter used in CAPD, one simply removes the tubular member by unscrewing it from its threaded, locked connection with the sleeve, to cause the universal connector to be ready to receive the luer lock connector. In the event a simple luer connection is desired, or a connection with a catheter end, one can slide the sleeve rearwardly to expose the luer taper section, for making that third type of connection.

The tubular member carried by the universal connector may carry a polygonal flange, for example a six-sided flange, transversely positioned on the tubular member and typically positioned adjacent the external threads to protect them as one handles the tubular member. Generally it is important to keep the external threads clean and free of contamination as the connection is made or broken, with the polygonal flange helping to provide this protection. Additionally, the polygonal flange prevents rolling of the tubular member when placed on a near-horizontal surface, while the tubular member having a round flange would tend to roll on a table that was not quite flat.

A second flange may also be provided adjacent the other end of the tubular member, to provide protection from the hand slipping over that end and depositing contamination in or near it and also to permit attachment with a connection shield or cover.

The sleeve may define an annular, free end, the internal threads being spaced from the free end to define an annular sealing area between the threads and free end. The free end then can enter into sealing relation with an annular enlargement of the structure to which it connects, to provide an annular sealing area in a manner similar to that described in U.S. Pat. No. 4,346,703.

DESCRIPTION OF THE DRAWINGS

In the drawings,

FIG. 1 is an elevational view, taken partly in longitudinal section, of the universal connector of this invention in its form capable of making connection with a spike-type connector.

FIG. 2 is a sectional view taken along line 2—2 of FIG. 1.

FIG. 3 is a sectional view taken along line 3—3 of FIG. 1.

FIG. 4 is an elevational view, taken partly in longitudinal section, of the universal connector of FIG. 1 in its configuration adapted for connection with a luer lock type connector.

FIG. 5 is an elevational view, taken partly in longitudinal section, of the universal connector of FIG. 1 in its configuration permitting connection with a simple luer type connector.

DESCRIPTION OF SPECIFIC EMBODIMENTS

Referring to FIGS. 1-3, universal connector 10 is disclosed. Connector 10 comprises a tubular connector 12 which is attached at one end to fluid flow conduit 14 and defines a luer taper tube portion 16 at its other end. Tubing 14 may be connected to any desired set or container, for example a container of peritoneal dialysis solution or a set for communication with a patient's peritoneal cavity for CAPD, IPD, or CCPD, to permit flow between the peritoneal cavity and peritoneal dialysis solution containers. Alternatively, the connector of this invention may be used in any other field desired, particularly the medical field for the delivery of medical solutions to a patient or from one sterile container to another.

Sleeve 18 is carried by and surrounds in a first position luer taper tube portion 16 as shown particularly in FIGS. 1 and 4. Sleeve 18 is longitudinally movable and typically relatively rotatable with respect to tubular connector 12 and luer taper portion 16. Sleeve 18 defines internal threads 20 which are provided for threaded, locking connection with another connector, specifically tubular connector 22, defining an end tubular section having external threads 24 which are in removable, threaded, locked connection with internal threads 20. Tubular member 22 defines at its other end an aperture 26 for sealingly receiving a spike connector through aperture 26 into sealing relationship with universal connector 10 when it carries tubular member 22. Member 22 may be made of molded plastic.

Tubular member 22 also defines, in this embodiment, a pair of flanges 36, 37 to provide protection of the ends of tubular member 22 from accidental contamination as one grasps member 22, the flanges serving to keep the fingers away from the ends. Also, flange 36, for example, may be made of polygonal shape as shown in FIG. 3 to prevent tubular member 22 from rolling on a slightly nonhorizontal table or other surface when it is separated from the rest of connector 12. Flange 37 may be grasped with a Connection Shield, sold be Travenol Laboratories, Inc., to lock the spike into connected relation with it.

Sleeve 18 defines stop members 28, which serve to limit the advance of sleeve 18 when they abut against flange 30 of tubular connector 12, so that sleeve 18 cannot be removed by forward pulling. Between flanges 28 are a pair of slots 32 into which projections 34 of connector 12 may fit when sleeve 18 is retracted as shown in FIG. 5.

As shown in the embodiment of FIG. 1, universal connector 10 is fitted for connection with a spike connector, which can sealingly pass into aperture 26. Thus it may connect with a spike on the end of the transfer set of a CAPD patient. Alternatively, it may connect with a spike of any other set or solution container as may be desired.

Referring to FIG. 4, in this configuration of use, universal connector 10 has had its connected tubular member 22 removed. This makes universal connector 10 capable of receiving a luer lock connector, for example, luer lock connector 38, which may be a titanium adapter of the type commonly used on the end of a peritoneal catheter 40 by CAPD patients. Luer lock connector 38 defines a set of forward external threads 42 proportioned to mate with internal threads 20 of movable sleeve 18. Accordingly, luer lock connector can be threaded into tight, sealing relation with sleeve 18. Sleeve 18 is retained in its position by the pressure of members 28 against flange 30, and the forward end of connector 38 may also press against flange 30 to provide a seal. Furthermore, another seal may be provided by the threadless free ends 44, which may telescopingly press against annular land 46 of luer lock connector 38 in a manner similar to that shown in U.S. Pat. No. 4,346,703. This provides a second seal above and beyond the seal naturally provided between luer taper portion 16 and the preferably correspondingly tapered bore of luer adapter 38, which provides a first inner seal in the conventional manner of a luer seal.

Thus, by the simple expedient of removing tubular member 22, universal connector 10 may be made adaptable for connection with a luer lock connector.

Referring to FIG. 5, the connector of this invention is shown in its configuration adapted for connection with a simple luer connector 48. Luer connector 48 may be connected to peritoneal catheter 50, a set for supplying solution in CDPD, or any other desired conduit which contains a luer connector.

As shown, sleeve 18 can slide rearwardly, with projections 34 on tubular connector 12 passing into slots 32 of sleeve 18, so that luer taper 16 is no longer surrounded by sleeve 18. This then provides space for luer taper 16 and luer connector 48, even if luer connector 48 does not fit within sleeve 18.

Also, engaging projections 34 provide rotational rigidity to sleeve 18 to help in breaking the luer connection, when that is desired.

Accordingly, the connector of this invention provides an inexpensive capability for connection with at least three different types of connectors. Thus sets, solution containers, or other devices that use the universal connector of this invention have a greatly increased flexibility of use, being connectable with different kinds of connectors for important advantages of use, and permitting the manufacturer of medical systems to simplify his inventory of sets, containers, and the like.

The above has been offered for illustrative purposes only, and is not intended to limit the scope of the invention of this application, which is as defined in the claims below.

That which is claimed is:

1. A universal connector for interconnecting a fluid flow conduit with either a threaded luer lock connector, a simple luer connector, or a spike connector, said universal connector comprising:

a tubular connector having an axis, said tubular connector being attachable at one end to the fluid flow conduit and having a luer taper tube portion at its axially opposite end;

a sleeve having internal threads and being carried by said tubular connector for movement along said axis between a first position, in which said sleeve encloses said luer taper tube portion, and a second position, in which said luer taper tube portion is exposed;

means operative, when said sleeve is in said first position, for permitting rotation of said sleeve about about enclosed luer taper tube portion to create, in response to the rotation of said sleeve, a removable threaded locking connection with the threaded luer lock connector, said means being alternately operative, when said sleeve is in said second position, for rotatably engaging said sleeve with said tubular connector to rotate said exposed luer taper tube portion along with said sleeve during the connection and disconnection of said exposed luer taper tube portion with the simple luer connector; and a tubular member mating at one end with said enclosed luer taper tube portion and having at said one end external threads forming a removable threaded, locked connection with said internal threads of said sleeve in response to rotation of said sleeve, said tubular member having at its other end means for sealingly receiving the spike connector.

2. The connector of claim 1 in which said tubular member defines a polygonal flange adjacent said external threads to protect said external threads as one handles the tubular member, and to prevent rolling of the tubular member when placed on a near-horizontal surface.

3. The connector of claim 1 in which said sleeve defines an annular free end, said internal threads being spaced from the free end to define an annular sealing area between the threads and free end.

4. The connector of claim 1 in which said tubular member defines a polygonal flange.

5. The connector of claim 4 in which said polygonal flange is adjacent one end of the tubular member and a second flange is positioned adjacent the other end of the tubular member.

6. The connector of claim 1 in which said tubular connector includes a retaining flange spaced from said luer taper tube portion, and said sleeve includes internal land means for engaging said retaining flange during movement of said sleeve from said second position toward said first position, thereby preventing removal of said sleeve from said tubular connector.

* * * * *